(12) United States Patent
Ouwerkerk et al.

(10) Patent No.: US 10,874,325 B2
(45) Date of Patent: Dec. 29, 2020

(54) SURFACE TREATMENT DEVICE AND METHOD

(71) Applicant: KONINKLIJKE PHILIPS N.V., Eindhoven (NL)

(72) Inventors: Martin Ouwerkerk, Eindhoven (NL); Lutz Christian Gerhardt, Eindhoven (NL); Neil Francis Joye, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 214 days.

(21) Appl. No.: 15/780,847

(22) PCT Filed: Dec. 14, 2016

(86) PCT No.: PCT/EP2016/081046
§ 371 (c)(1),
(2) Date: Jun. 1, 2018

(87) PCT Pub. No.: WO2017/102867
PCT Pub. Date: Jun. 22, 2017

(65) Prior Publication Data
US 2018/0353101 A1 Dec. 13, 2018

(30) Foreign Application Priority Data
Dec. 15, 2015 (EP) ..................... 15200205

(51) Int. Cl.
*A61B 5/053* (2006.01)
*A61B 5/00* (2006.01)
(Continued)

(52) U.S. Cl.
CPC ............ *A61B 5/0531* (2013.01); *A61B 5/068* (2013.01); *A61B 5/442* (2013.01); *A61B 17/54* (2013.01);
(Continued)

(58) Field of Classification Search
CPC .......... A61B 17/54; A61B 2017/00398; A61B 2017/00747; A61B 2017/00761;
(Continued)

(56) References Cited

U.S. PATENT DOCUMENTS 4,274,419 A 6/1981 Tam
2004/0230227 A1 11/2004 Avrahami
(Continued)

FOREIGN PATENT DOCUMENTS

WO 2013177126 A2 11/2013
WO 2014136013 A1 9/2014
WO 2014191149 A1 12/2014

OTHER PUBLICATIONS

Ya Yang et al., "Human Skin Based Triboelectric Nanogenerators for Harvesting Biomechanical Energy and as Self-Powered Active Tactile Sensor System", 2013, Acsnano, vol. 7, p. 1-10 (Year: 2013).*

(Continued)

*Primary Examiner* — Katherine M Shi
*Assistant Examiner* — Alyssa M Keane

(57) ABSTRACT

A sensor is provided for sensing layer removal from a surface. A head has an abrasive portion for contacting the surface and a conducting portion inside the head. This device has a sensor design which provides self-generation of a sensor signal with no power supply to the device head. This simplifies the design of the sensor head, and means it can have a design which is easy to clean with no parts which are easily damaged. In one set of examples, the device is a skin treatment device.

19 Claims, 4 Drawing Sheets

(51) Int. Cl.
  A61B 17/54 (2006.01)
  A61B 5/06 (2006.01)
  A61B 17/00 (2006.01)
  A61B 17/32 (2006.01)
  A61B 18/00 (2006.01)
  A61B 90/00 (2016.01)
  A61B 18/12 (2006.01)

(52) U.S. Cl.
  CPC ........... *A61B 2017/00026* (2013.01); *A61B 2017/00398* (2013.01); *A61B 2017/00747* (2013.01); *A61B 2017/00761* (2013.01); *A61B 2017/320004* (2013.01); *A61B 2018/00452* (2013.01); *A61B 2018/00642* (2013.01); *A61B 2018/1226* (2013.01); *A61B 2090/062* (2016.02); *A61B 2562/0214* (2013.01)

(58) Field of Classification Search
  CPC ......... A61B 2017/320004; A61B 2018/00452; A61B 2018/00642; A61B 2018/1226; A61B 2090/062; A61B 2562/0214; A61B 5/0531; A61B 5/068; A61B 5/442
  See application file for complete search history.

(56) References Cited

U.S. PATENT DOCUMENTS

| | | | |
|---|---|---|---|
| 2008/0275378 A1 | 11/2008 | Herndon | |
| 2008/0275468 A1* | 11/2008 | Chuang | A61B 5/442 606/131 |
| 2008/0287767 A1 | 11/2008 | Pasveer | |
| 2014/0300248 A1* | 10/2014 | Wang | H02N 1/04 310/300 |
| 2014/0378887 A1* | 12/2014 | Chang | A61N 1/0472 604/20 |

OTHER PUBLICATIONS

Ya Yang et al, "Human Skin based Triboelectric Nanogenerators for Harvesting Biomechanical Energy and as Self-Powered Active Tactile Sensor System", ADS Nano, vol. 7, 10, Oct. 22, 2013, p. 9213-0222.

A.F. Diaz and R.M. Felix-Navarro, "A semi-quantitative triboelectric series for polymeric materials: the influence of chemical structure and properties", Journal of Electrostatics 62 (2004) 277-290.

T. Yamamoto and Y. Yamamoto, Electrical properties of the epidermal stratum corneum, Medical and Biological Engineering, (Mar. 1976), pp. 151-157.

Ju-Hyuck Lee et al: "Control of Skin Potential by Triboelectrification with Ferroelectric Polymers", Advanced Materials, vol. 27, No. 37, Oct. 20, 2015 (Oct. 20, 2015), pp. 5553-5558, XP055347899, DE ISSN: 0935-9648, DOI: 10.1002/adma.201502463 the whole document.

Lokesh Dhakar, Prakash Pitchappa, Francis Eng Hock Tay, Chengkuo Lee, "An intelligent skin based self-powered finger motion sensor integrated with triboelectric nanogenerator", Nan Energy, vol. 19, Jan. 2016, pp. 532-540.

Lokesh Dhakar, F.E.H. Tay, and Chengkuo Lee, "Skin based flexible triboelelctric nanogenerators with motion sensing capability", MEMS 2015, pp. 106-109.

C. Pailler-Mattei, C. Guerret-Piecourt, H. Zahouani, S. Nicoli, Journal of the royal society interface, Interpretation of the human skin biotribological behaviour after tape stripping; J Royal Soc Interface, 8 934-941, Jan. 12, 2011.

B. Meng, X.L. Cheng, M.D. Han, H.T. Chen, F.Y. Zhu and H.X. Zhang, "Triboelectrification based active sensor or polymer distinguishing", Micro Electro Mechanical Systems (MEMS), 2015 28th IEEE International Conference, pp. 102-105.

\* cited by examiner

SURFACE TREATMENT DEVICE AND METHOD

This application is the U.S. National Phase application under 35 U.S.C. § 371 of International Application No. PCT/EP2016/081046, filed on Dec. 14, 2016, which claims the benefit of International Application No. 15200205.1 filed on Dec. 15, 2015. These applications are hereby incorporated by reference herein.

FIELD OF THE INVENTION

The present application relates to a surface treatment device, in one particular set of examples it relates to a microdermabrasion device. The present application also relates to a method of determining the operating depth of surface abrasion. Yet further, the invention also relates to a sensor that may be used in the treatment device or for the method.

BACKGROUND OF THE INVENTION

WO2013/177126 describes an electrode assembly array for use in Electrical Impedance Tomography (EIT), the electrode assembly array comprising a plurality of electrode assemblies mounted to a frame, the electrode assemblies comprising an electrode for contacting a subject and a drive element, the drive element adapted to drive the electrode towards the subject from the frame for contacting the subject and an abrasion element adapted to move the electrode such that it abrades the subject.

US2008/275378 describes an apparatus that creates a number of microconduits, i.e., small holes in the stratum corneum, the outermost layer of human skin tissue, to provide a pathway therethrough, which can be used, for example, for transdermal drug delivery.

Ya Yang et al., Human Skin Based Triboelectric Nanogenerators for Harvesting Biomechanical Energy And As Self-Powered Active Tactile Sensor System, ACS Nano, vol. 7, no. 10, 22 October 2013, p. 9213-9222 describes human skin based triboelectric nanogenerators (TENG) that can either harvest biomechanical energy or be utilized as a self-powered tactile sensor system for touch pad technology. They constructed a TENG utilizing the contact/separation between an area of human skin and a polydimethylsiloxane (PDMS) film with a surface of micropyramid structures, which was attached to an ITO electrode that was grounded across a loading resistor. The fabricated TENG delivers an opencircuit voltage up to 1000 V, a short-circuit current density of 8 mA/m$^2$, and a power density of 500 mW/m$^2$ on a load of 100 MΩ, which can be used to directly drive tens of green light-emitting diodes. The working mechanism of the TENG is based on the charge transfer between the ITO electrode and ground via modulating the separation distance between the tribo-charged skin patch and PDMS film. Furthermore, the TENG has been used in designing an independently addressed matrix for tracking the location and pressure of human touch. The fabricated matrix has demonstrated its self-powered and high-resolution tactile sensing capabilities by recording the output voltage signals as a mapping figure, where the detection sensitivity of the pressure is about 0.29 (0.02 V/kPa and each pixel can have a size of 3 mm×3 mm. The TENGs may have potential applications in humanmachine interfacing, micro/nano-electromechanical systems, and touch pad technology.

US2004/0230227 describes a device for treating skin on the body of a subject. The device includes a plurality of electrodes, which are adapted to be placed in contact with the skin and then moved across the skin while maintaining electrical contact with the skin.

The device additionally includes a power source, which is adapted to apply a current between two or more of the plurality of electrodes at the same time as the electrodes are being moved across the skin.

US2008/275468 describes devices, systems, kits and methods for increasing the skin's permeability controlled by measured skin electrical parameter. They may be used for transdermal drug delivery and/or analyte extraction or measurement. The controlled abrasion device contains (i) a hand piece, (ii) an abrasive tip, (iii) a feedback control mechanism, (iv) two or more electrodes, and (v) an electrical motor. The feedback control mechanism may be an internal feedback control mechanism or an external feedback control. The kit contains the controlled abrasion-device, one or more abrasive tips, optionally with a wetting fluid. The method for increasing the skin's permeability requires applying the controlled abrasion device to a portion of the skin's surface for a short period of time, until the desired level of permeability is reached. Then the abrasion device is removed, and a drug delivery composition or device or an analyte sensor is applied to the treated site.

WO 2014/136013 describes a microdermabrasion device. The device has a suction path along which skin fragments removed by the device are drawn, and a detection unit configured to determine one or more characteristics of skin fragments drawn along the suction path. The detection unit is configured to determine the depth of abrasion performed by the device based on the one or more characteristics of skin fragments drawn along the suction path. The present application also relates to a method of determining the operating depth of abrasion of a microdermabrasion device.

SUMMARY OF THE INVENTION

It is known to provide exfoliation of skin as a light cosmetic procedure. Such a procedure is used to remove dead cells from the outermost layer or layers of the skin. This provides a means of rejuvenating the skin, clearing pores and minimizing lines and other marks found on the surface of skin.

One such procedure used to remove dead cells from the outermost layer or layers of the skin is microdermabrasion. Microdermabrasion uses a mechanical medium for exfoliation to remove dead skin cells from the outermost layer or layers of skin, referred to as the epidermis. Benefits include epidermal thickening and collagen deposition.

Microdermabrasion devices generally comprise two parts: an abrasive material to act on and remove the outermost layer or layers of skin; and a suction means to gently lift up and stretch the skin which brings oxygen and nutrients to the surface, encouraging blood circulation in the dermis. Due to the (enhanced) blood circulation, (more) oxygen and/or nutrients can be brought to the surface, which may be beneficial for the skin.

Microdermabrasion devices work by either loose particle abrasion or fixed surface abrasion. With loose particle abrasion, a high pressure stream of particles, such as aluminum oxide, magnesium oxide, sodium chloride, or sodium bicarbonate particles are directed towards the skin to abrade the skin and remove skin fragments from the upper layer or layers of skin. A vacuum is also produced to remove the abrasive particles and exfoliated skin fragments from the area of the skin.

In fixed surface abrasion, a roughened surface, such as a diamond grit-embedded surface or aluminium oxide particle-coated surface, is moved over the skin to abrade the skin and remove skin fragments from the upper layer or layers of skin.

The skin has two primary layers—the epidermis and the dermis. The epidermis comprises the outermost layers of the skin. Such layers include the stratum corneum (the outermost layer), the stratum lucidum, stratum granulosum, stratum spinosum, and stratum basale. It has been found that removal of the stratum corneum at least aids the beneficial results of microdermabrasion. Therefore, it is necessary to ensure that a suitable depth of abrasion is applied to the skin. However, it has also been found that if the depth of abrasion exceeds a certain level then irritation of the skin or bleeding may occur.

It is known to attempt to achieve a desired depth of abrasion of the skin by applying a predetermined number of passes of the microdermabrasion device to the skin. However, such a method is inaccurate and does not take into account other variables such as different skin types, location of the skin and condition of the skin.

While exfoliation devices work very effectively, there is generally no feedback mechanism to indicate to the user how much more treatment is appropriate. This would be desirable in order to provide a warning before skin irritation or damage may result.

There is therefore a need for a simpler system for determining (amongst others e.g.) the abrasion depth of a skin treatment device, and for depth determination for surface abrasion processes generally.

The present invention proposes such skin treatment device. Further the invention also provides a sensor. Yet further, the invention provides a method for determining an amount of layer removal from a surface, especially a skin, during an abrasive process, especially with the device as described herein. The invention is defined by the claims.

In a first aspect, the invention provides a (skin) treatment device ("device") comprising: a head with an abrasive portion for contacting a (skin) surface and a conducting portion; a sensor for sensing layer removal from the (skin) surface, the sensor comprising said conducting portion, a handle electrode, and a voltage circuitry for measuring a voltage between said conducting portion and said handle electrode. Herein, the invention is further defined in relation to abrasion of the skin. The device used may herein also be indicated as "skin treatment device", or "device", but may also be indicated as "microdermabrasion device".

With such device, in a relatively easy way the abrasion can be monitored as the voltage circuitry may measure the voltage difference between the the conductive portion and the counter electrode or handle electrode (generated by the triboelectric effect and the resistance of the (skin) surface). The measured voltage difference, or other electrical property, may be related to an extend of abrasion. Hence, the device may also include a controller that may monitor the abrasion process and/or surface abrasion and/or surface properties (with the voltage circuitry). Further, the controller may be configured to control the skin treatment device as function to a signal of the voltage circuitry (such as a voltage difference, or a change in voltage, etc.), and may e.g. reduce or include an underpressure of the device when the device includes a suction channel and/or a flux of abrasive particles to the surface when abrasive particles are used that are not bound to the abrasive portion and/or a rotation, vibration or oscillation when a device is applied that has an abrasive portion that may rotate, vibrate or oscillate.

In embodiments, the abrasive portion may physically isolate the conduction portion from the surface. In this way, during use of the device, the conduction portion can not physically get into contact with the surface. Hence, in embodiments the conduction portion is shielded by a non-conduction portion, and the conduction portion is configured not to be in physical contact with the user during use of the skin treatment device. For instance, the abrasive portion may include an electrically non-conductive material, such as a non-conductive ceramic material. In this situation, the conducting portion acts as a passive induction electrode. Hence, in embodiments the conducting portion may be configured on the backside of the abrasive portion (with the front side of the abrasive portion being abrasive). The conduction portion is especially, however, comprised by the head. The head may be configured in removable association with the device.

In yet other embodiments, the conduction portion may come into physical contact with the surface during use of the device. In such embodiments, especially the conduction portion comprises said abrasive portion. Hence, in embodiments the conduction portion, or at least part thereof, is configured as abrasive portion.

The device is especially a handheld device. Therefore, especially the (counter) electrode for measuring e.g. a potential difference with the conductive portion is herein also indicated as "handle electrode". Especially, the handle electrode is configured to be in electrical contact with the user during use of the skin treatment device. Hence, the handle electrode may comprise a portion of the device surface. Of course, the handle electrode is not in physical contact with the conductive portion. The handle electrode may be in electrical contact with the conductive portion via the voltage circuitry. The voltage circuitry may include a potentiometer, such as a high impedance voltage meter ($>10^{11}\Omega$) (see also FIG. 5). The handle electrode may during use (thus) be in contact with a hand of the user, especially the flat (palm) of the hand, while the abrasive portion is (at least temporarily) in contact with the (skin) surface. In specific embodiments, the handle electrode has an area selected from the range of 2-250 cm$^2$, such as 10-250 cm$^2$. For instance, the area may be selected from the range of 4-100 cm$^2$, like 10-40 cm$^2$. Hence, in embodiments during use the abrasive portion is at least temporarily in contact with the skin of a user and the handle contact is in physical contact with flat (palm) of the hand while the abrasive portion is (at least temporarily) in contact with another part of the (skin) surface, such as the face, the chest, an arm, a leg, intimate grooming parts, etc.

In embodiments, the skin treatment device further comprises a suction system. The suction may in embodiments be controlled in response to a signal of the voltage circuitry. Thereby, the skin treatment device, especially the suction system, may be controlled as function to a signal of the voltage circuitry.

Further examples in accordance with an aspect of the invention provide a sensor for sensing layer removal from a surface, comprising: a head with an abrasive portion for contacting the surface and a conducting portion; and a generator for generating charge in response to movement of the abrasive portion over the surface, wherein the generator is used as a sensor for measuring a parameter which is dependent on the level of layer removal, the sensor signal comprising the charge generated by the generator.

This sensor makes use of charge generation during an abrasion process to measure the level of layer removal caused by the abrasion. The sensor may be used in any handheld device and it suitable for sensing layer removal from surfaces. Such a device can be a device which senses removal of one insulating layer from another.

The use of charge generation enables sensing with no power supply to the abrasive portion (which functions as the sensor area). This simplifies the design of the sensor, and means it can have a design which is easy to clean with no parts which are easily damaged. The sensor is in embodiments simply formed by the abrasive portion, without the need for additional external sensor parts which may add unacceptable volume, complexity and cost to a small hand held abrasive device.

The abrasive portion may be at the external surface of the head, and the conducting portion may be a separate component inside the head.

The generator preferably comprises a triboelectric generator. Sensing removal of one material, such as an insulating dielectric material, from another material, again such as a dielectric support, can reliably be sensed due to the difference in triboelectric properties. For example, a thin polymer coating may be provided on a dielectric substrate. The removal of the polymer coating may be difficult to measure with other sensor principles such as resistive or capacitive sensing approaches. A conductive (or even semiconductive) layer removal may also be detected from a dielectric insulating layer.

Instead of a triboelectric system, the charge generation may be based on electrostatic charge generation or charge induction. For example charges may be sprayed on the surface.

The generator may in one preferred example comprise a single-electrode triboelectric generator.

The conducting portion for example comprises a metallic disc which functions as a passive induction electrode. However, the conduction portion and the abrasive portion may be the same component (i.e. a conducting abrasive material).

The sensor or device may comprise a voltage measuring circuit for measuring a voltage between the conducting portion of the abrasive head and the surface. This voltage is generated by charge injection from the triboelectric generator into the capacitance between the head of the device and the surface.

The sensor or device may (additionally or alternatively) comprise a voltage rate measuring circuit for measuring a rate of change of the voltage between the conducting portion of the abrasive head and the surface. This may provide a more accurate indication of the insulating property.

The device may comprise a capacitance measuring circuit for measuring a capacitance between the conducting portion of the abrasive ring and the surface.

In one set of examples, the sensor comprises a skin sensor for sensing skin layer removal, and the dielectric skin layer is the skin surface. The skin itself is then used as part of the overall sensor and forms part of a floating sensing device with self-generation of a sensor signal.

The invention also provides a skin treatment device, comprising a skin sensor as defined above, wherein the abrasive portion is an abrasive ring for contacting the skin. The device may further comprise a suction system for bringing oxygen and nutrients to the skin surface.

The abrasive ring may be an embodiment of a microdermabrasion zone. Hence, the microdermabrasion zone may be configured as ring (see also below wherein the ring may comprise a rim). The ring is not necessarily round, but may also be oval. Further, the microdermabrasion zone (or microdermabrasion area) may comprise a single part, but may also comprise two (or more) parts that from the microdermabrasion zone, and which may in embodiments be together configured as ring.

The device preferably comprises a handle having an electrical handle contact ("handle electrode") which is thereby at the potential of the user. This provides the reference against which the generated/induced voltage at the conducting portion of the head can be compared. The handle contact area may in embodiments have an area of between 10 and 250 square centimeters. This assists in reducing disturbance to measurement of the charge generated by the triboelectric effect.

The device may further comprise an output device and a controller for controlling the output device, which is adapted to provide an output warning when the skin treatment should be ceased based on the measured parameter.

In this way, skin irritation can be prevented by advising a user when to move to a different skin area.

Examples in accordance with another aspect of the invention provide a method of determining an amount of layer removal from a surface during an abrasive process, comprising: contacting the surface with an abrasive head of an abrasion device; moving the head over the surface and thereby generating charge in response to the movement; and using the charge generated as a sensor signal for measuring a parameter which is dependent on the level of layer removal.

This method provides the generation of charge from the movement of an abrasion device, and uses this charge for layer removal sensing. This provides a compact design with few additional components needed to implement a sensing function.

Measuring a parameter may comprise measuring a voltage between a conducting portion inside the device head and the surface, or measuring a rate of change of the voltage between the conducting portion inside the device head and the surface or measuring a capacitance between the conducting portion inside the device head and the surface.

The method may be for determining an amount of skin removal during a skin treatment, wherein the surface comprises the skin. The method may then further comprise providing an output warning when the skin treatment should be ceased based on the measured parameter.

The charge is for example generated by triboelectrification.

The method may further comprise providing a calibration to determine the level of the parameter before the skin treatment begins and when the treatment should stop.

Amongst others, the following embodiments are provided, which are—for the ease of reference—numbered: Embodiment 1: A sensor for sensing layer removal from a surface, comprising: a head with an abrasive portion for contacting the surface and a conducting portion; and a generator for generating charge in response to movement of the abrasive portion over the surface, wherein the generator is used as a sensor for measuring a parameter which is dependent on the level of layer removal, the sensor signal comprising the charge generated by the generator. Embodiment 2: A sensor as described in embodiment 1, wherein the generator comprises a triboelectric generator. Embodiment 3: A sensor as described in embodiment 2, wherein the generator comprises a single-electrode triboelectric generator. Embodiment 4: A device as described in any preceding embodiment, wherein the conducting portion comprises a metallic disc which functions as a passive induction electrode. Embodiment: 5: A device as described in any preceding embodiment, comprising: a voltage measuring circuit ("voltage circuitry") for measuring a voltage between the conducting portion of the abrasive head and the surface; and/or a voltage rate measuring circuit for measuring a rate of change of the voltage between the conducting portion of the abrasive head and the surface. Embodiment 6: A sensor as described in any preceding embodiment, comprising a skin sensor for sensing skin surface removal, and the layer is the skin surface. Embodiment 7: A skin treatment device, comprising: a sensor as described in embodiment 6, wherein: the abrasive portion is an abrasive ring for contacting the skin. Embodiment 8: A device as described in embodiment 7, further comprising a suction system for bringing oxygen and nutrients to the skin surface. Embodiment 9: A device as described in embodiment 7 or 8, wherein the device comprises a handle having an electrical handle contact which is thereby at the potential of the user. Embodiment 10: A device as described in embodiment 9, wherein the handle contact electrode has an area of between 10 and 250 square centimeters. Embodiment 11: A device as described in any one of embodiments 6 to 10, further comprising: an output device; and a controller for controlling the output device, which is adapted to provide an output warning when the skin treatment should be ceased based on the measured parameter. Embodiment 12: A method of determining an amount of layer removal from a surface during an abrasive process, comprising: contacting the surface with an abrasive head of an abrasion device; moving the head over the surface and thereby generating charge in response to the movement; and using the charge generated as a sensor signal for measuring a parameter which is dependent on the level of layer removal. Embodiment 13: A method as described in embodiment 12, wherein measuring a parameter comprises: measuring a voltage between a conducting portion of the abrasive head and the surface; and/or measuring a rate of change of the voltage between a conducting portion of the abrasive head and the surface. Embodiment 14: A method as described in embodiment 13, further comprising providing an output warning when the skin treatment should be ceased based on the measured parameter. Embodiment 15: A method as described in embodiment 13 or 14, comprising generating the charge by triboelectrification.

In an aspect, the invention provides a skin treatment device comprising a sensor for sensing layer removal from a surface, comprising: a head with an abrasive portion for contacting the skin surface and a conducting portion, as well as a hand (contact) electrode; whereas the sensor—formed by the features (conducting portion and handle electrode (and optionally the abrasive portion)—measures generated charges in response to movement of the abrasive portion over the surface, and this generated sensor signal is used for measuring a parameter which is dependent on the level of layer removal, wherein the sensor comprises a selfpowered single-electrode triboelectric generator configuration.

The "micro dermo abrasion" or "mircodermabrasion" (MDA) technique is being used to help the upper skin layer (the so called stratum corneum) to renew in a faster way than it would normally do. Traditionally, crystal microdermabrasion system contains a pump, a connecting tube, a hand piece, and a vacuum source. While the pump creates a high-pressure stream of inert crystals, like aluminum oxide, to abrade the skin, the vacuum removes the crystals and exfoliated skin cells. Instead of abrasion with particles in a gas stream, also a roughened surface, such as a diamond surface, of the tip of the device can be used. This is for instance known as (diamond) microdermabrasion. Unlike the crystal microdermabrasion system, the (diamond) microdermabrasion does not produce particles from crystals that may be inhaled into patients' nose or blow into the eyes.

The present invention especially relates amongst others to a microdermabrasion device with a stationary abrasion zone (i.e. no moving abrasive part) and to microdermabrasion devices which use the abrasion zone as abrasive means, thus without the use of (a flow of) abrasive particles that (is) are used to abrade the skin and may be sucked by the vacuum. However, in other embodiments, the present invention also relates to a microdermabrasion device wherein the microdermabrasion area may be moving (i.e. not stationary) and/or wherein (a flow of) abrasive particles (is) are applied.

As indicated herein, in embodiments of this invention the vacuum may be controlled in response to a signal of the voltage circuitry. The control of the vacuum or underpressure to the inlet zone may be executed in several ways. In an embodiment, the controller changes the vacuum provided by a pump (directly). For instance, the power supply to the pump may be controlled. Additionally or alternatively, one may keep e.g. the pump at a constant level, but control a leakage of the vacuum.

The vacuum system comprises a channel with a channel inlet (or "channel opening") at an inlet zone. The channel is in fluid connection with the pump (for creating the vacuum) and the inlet zone. Further, the channel may be in fluid communication with the (optional) bypass system. The vacuum system is thus especially controllable in the sense that the underpressure may be adaptable at a plurality of pressures (see also below for pressures), such as e.g. a stepwise controllable underpressure. The vacuum system is herein also indicated as "suction system".

The vacuum system may comprise a source of vacuum, such as pump, configured to provide a suction flow in a direction from the channel inlet to the source of vacuum, such as a pump. The channel inlet or inlet zone, which is at the device tip, is thus configured upstream of the vacuum pump. Especially, the device may be configured to provide a negative pressure ("underpressure") in the range of 5-80 kPa, such as especially 15-60 kPa, such as in the range of 20-40 kPa. This may especially imply that when the skin is in contact with the inlet zone, and closes off the inlet zone, the device is able to provide a pressure which is in the range of 15-60 kPa lower than atmospheric pressure. Hence, the term underpressure may especially indicate that when the skin is in contact with the inlet zone, the skin may be sucked at least partly into the inlet zone due to the suction of the vacuum system, leading to an underpressure in the inlet zone relative to ambient pressure. Hence, especially the vacuum system is configured to suck gas from the inlet zone away into the vacuum system.

In general, the inlet zone is configured in such a way, that a good closing connection with the skin may be achieved. Especially, the inlet zone comprises a rim, herein also indicated as "channel rim". This channel rim may be a (slightly) protruding part of the device tip. The channel rim may also be seen as a distal part or end part of the channel opening. Especially this rim will be in contact with the skin of a user during use of the device. Optionally, this rim may comprise the microdermabrasion area with abrading material.

The controller may include a temporary memory. Optionally, the controller also comprises a (remote) permanent memory for storage of sensor signal information. In this way, e.g. the controller may generate a map of at least part of a human skin. In this way, it is also possible to derive information on skin (treatment) progress, or deterioration, on the basis of which the controller may further adapt the vacuum setting. Further, the controller may store treatment information, such as the vacuum conditions and time used for the treatment. Based thereon, the controller may be configured to suggest further treatment. For instance, the microdermabrasion device may give instruction to stop treating a specific zone or to continue treatment of a specific zone. Such information may be provided on a display and/or may be provided via a sound signal and/or may be provided via a vibration signal. The display and (graphical) user interface may be integrated in a single unit. Hence, sensor signal information, as well as development over time, and conclusions thereon, may e.g. be displayed on a display of the sensor device (or with the App; see also above). Hence, in yet a further embodiment the controller is configured to store one or more of (a) sensor signal information, and (b) treatment information, and the controller is further configured to execute one or more of (i) controlling the vacuum as function of one or more of said sensor signal information and treatment information, and (ii) providing on a display information retrieved from one or more of said sensor signal information and treatment information.

There are a number of types of microdermabrasion devices.

For instance, abrasive particles may be used that are propelled by a gas flow to the skin (in or in front of the inlet zone) and thereby abrade the skin, or the microdermabrasion device comprises an area with abrasive material, which has an abrasive function when the microdermabrasion device is moved over the skin. In the former embodiment, the abrasive material comprises abrasive particles, which are provided in a flow, and in the latter embodiment, the abrasive material is immobilized, and e.g. comprised by a rim.

Optionally, the microdermabrasion device may also include a moving, such as rotating, element including abrasive material (especially a moving microdermabrasion zone). In such embodiment, the abrasive material is also immobilized, and may e.g. comprised by a movable element, such as a rotatable rim. In embodiments, the terms "rotation" or "rotating" may optionally also refer to "oscillation" or "oscillating". Hence, in embodiments the term "rotation" and similar terms refer to full rotations, and in other embodiments the term "rotation" and similar terms refer to rotations less than 360° among a rotational axis.

Of course, also combinations of two or more embodiments may be applied.

In principle, for all these embodiments the invention may be useful, as in all cases a vacuum may be used to remove the material that is abraded, and optionally also for massage properties. Hence, in a specific embodiment the microdermabrasion device further comprises an abrading material system configured to provide in a gas flow abrading material to the microdermabrasion zone. The terms "abrasive material" and "abrading material" may substantially refer to the same material; particle properties of embodiments of such materials are defined below (see e.g. information concerning "particulate material"). Alternatively, (or optionally additionally), the microdermabrasion zone (of the microdermabrasion device) comprises a microdermabrasion area comprising immobilized abrading material.

Especially, the channel opening (with its channel rim) is configured such that a suitable vacuum area is obtained. The channel opening, especially the channel rim has (or provides) a vacuum area in the range of 10-400 mm$^2$, such as 10-200 mm$^2$, such as at least 20 mm$^2$, like especially at least 45 mm$^2$, especially in the range of 45-75 mm$^2$, such as especially 50-75 mm$^2$. This vacuum area is especially the area enclosed by the channel rim. It is especially also the (cross-sectional) area of the inlet zone.

As indicated above, the abrasion zone has abrasive properties, such as due to microscopic structures that facilitate abrasion of the upper part of the skin. Such microscopic structures may for instance be selected from the group consisting of alumina structures, such as particles, and diamond structures, such as diamond particles. These structures are comprised by the abrasion rim, i.e. are attached or part of the rim. Especially, the microdermabrasion area comprises abrasive structures, such as particulate material, attached to the microdermabrasion area having mean dimensions in the range of 1-1000 µm, such as 2-300 µm, like 5-80 µm or 120-200 µm. These dimensions may also apply when a gas flow with abrading particles is applied. Alternatively or additionally, the microscopic structures may for instance be selected from the group consisting of silicon carbide structures, such as silicon carbide particles, and metal nitride structures, such as metal nitride particles. Alternatively or additionally, the microscopic structures may for instance be selected from the group consisting of metal oxide structures, such as aluminum oxide particles and aluminum oxide structures. Further options of microscopic structures may for instance be selected from the group consisting of diamond structures, boron nitride structures, silicon carbide structures (see also above), glass beads, steel grit structures, other metal grit structures, zirconium oxide structures, and quartz structures. Combinations of different kind of structures, both in chemical composition and/or dimensions, may also be applied. In an embodiment, the quotient of the number of abrasive particles at the channel rim is especially 10% or less, more especially 5% or less, even more especially 1% or less of the number of abrasive particles comprised by the microdermabrasion area, especially 0.1% or less. In an embodiment, such abrasive particles are not comprised at all by the channel rim. The lower content or absence of such particles by the channel rim may facilitate gliding. The numbers given here as especially provided as an indication for certain embodiments to indicate the difference between the functionality of the channel rim and the microdermabrasion area.

The abrasive particles are especially available in the microdermabrasion area in a density in the range of 20-500 particles/mm$^2$. Especially particles in the size of 2-200 µm are available in this density (either mobile or immobilized in a microdermabrasion area). As indicated above, the channel ring or gliding, and the optional second gliding zone (see further below), have substantially no abrasive particles, or, as indicated above, especially 10% or less, more especially 5% or less, even more especially 1% or less of the number of abrasive particles comprised by the microdermabrasion area. Hence, assuming e.g. the microdermabrasion area having 250 particles of with one or more dimensions in the range of 100 µm per mm2, the number of such particles at the gliding zone(s) may be in the range of 25/mm$^2$ or lower (respectively). The abrasive particles may e.g. be glued to a surface, to provide the microdermabrasion area. However, alternative options are also possible. An abrasive surface can be made in many ways. Abrasive particles may be glued or metal plated. An abrasive structure can also be made from a solid material by machining or sanding a material. A surface treatment by a laser is also possible. Also by inject molding an abrasive surface can be created.

In an embodiment, the microdermabrasion area is stationary, i.e. especially the microdermabrasion area is not configured to move relative to the device. In yet another embodiment, the microdermabrasion area may be able to move. For instance, the device may be configured to let the microdermabrasion area vibrate. Optionally or additionally, the device may be configured to let the microdermabrasion area rotate. Such rotation may also include a vibration movement, for instance when the rotation is only a small rotation hence and forth (see also above when describing "oscillation").

With such MDA device, at least part of the stratum corneum can be removed from the skin of a human. This can be done in a non-therapeutical treatment, such as a cosmetic treatment. Hence, the invention also provides a method for the controlled removal of at least part of the stratum corneum, the method comprising contacting the microdermabrasion device as defined herein with part of a skin and removing at least part of the stratum corneum while applying a vacuum to the vacuum channel. An advantage of the method and device of the invention is also that it (they) can be used for reducing a lateral force (gliding force) that has to be applied by a user when removing at least part of the stratum corneum with said device. Alternatively or additionally, the method and/or device as described herein can be used for reducing lateral force (gliding force) when removing at least part of the stratum corneum with said device. Further, alternatively or additionally, the method and/or device as described herein can be used for reducing a lateral force that has to be applied by a user when removing at least part of the stratum corneum with said device. Alternatively or additionally, the method and/or device as described herein can be used for increasing the treatment efficiency while not substantially increasing the vacuum level, keeping the same vacuum level, or even reducing, the vacuum level. Alternatively or additionally, the method and/or device as described herein can be used for increasing the treatment are while not substantially increasing, or even reducing, the gliding force. In yet a further aspect, the device and method may also be used in or for a therapeutic treatment.

Further variants and embodiments described in WO2014191149 may also be used in combination with the present invention. WO2014191149 is herein incorporated by reference.

The device is especially a handheld device. Hence, the device may be designed to be used while being held in a single hand. Hence, the weight of the device is especially equal to or less than 1.75 kg, such as equal to or less than 1 kg, like in the range of 200-700 gram.

Amongst others, this invention provides a sensor device that measures the rate and amount of skin exfoliation during a treatment with a skin rejuvenation device. When the level of exfoliation is reached that offers an optimal balance between rejuvenation and the prevention of skin irritation (skin rash) a signal tells the end user to move on to the next untreated piece of skin. The sensor principle is based on the triboelectric effect and capacitive coupling. The rubbing of the rejuvenation device against skin causes an electrical charge build-up. The charge leaks away through the skin. The rate of this process depends on the skin conductance. The stratum corneum is a resistive barrier in for the skin conductance. Exfoliation of the stratum corneum lowers this barrier, causing the triboelectric charges to leak away faster. A metal ring head (also in general referred to as the conducting portion) inside the rejuvenation a device responds to the surface charge build-up by means of capacitive coupling. A high impedance voltage meter ($>10^{11}\Omega$) is used to measure the potential difference between the metal ring and the end user. A metal hand contact on the handle of the skin rejuvenation device ensures a low resistance electrical contact to the end user. The size of this contact needs to be sufficient as not to disturb the measurement of the tribo charge. For example a size of 10 to 50 centimeter squared can be sufficient. The height of the voltage peaks in this sensor circuit caused by the triboelectric effect brought about by the scrubbing of the device against the skin is a measure of the exfoliation of the skin. When the peak is lowered by a pre-set percentage a signal is given to the end user to move on to the next skin spot.

In a more sophisticated embodiment the time derivative of ascending slope of the voltage signal is used as a measure of stratum corneum removal. The time derivative of the voltage of the ascending slope is diminishing when the stratum corneum is removed since it is the sum of a charge build-up by the triboelectric effect brought about by a rubbing movement and the leaking away of charge through the upper skin layers to the body. This is true assuming the rubbing actions to have equal speed and pressure. The distance of the rubbing action is no longer a parameter if the time derivative is used.

BRIEF DESCRIPTION OF THE DRAWINGS

Examples of the invention will now be described in detail with reference to the accompanying drawings, in which.

DETAILED DESCRIPTION OF THE EMBODIMENTS

Figure 1:
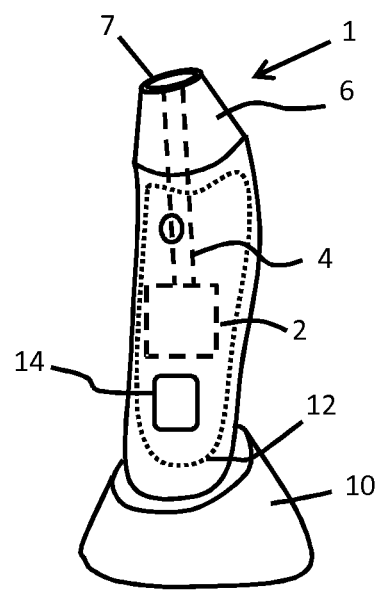
FIG. 1 shows a skin treatment system.

The invention provides a sensor for sensing layer removal from a surface. A head has an abrasive portion for contacting the surface and a conducting portion. A generator is used for generating charge in response to movement of the abrasive portion over the surface. The generator is used as a sensor for measuring a parameter which is dependent on the level of layer removal, the sensor signal comprising the charge generated by the generator.

This device has a sensor design which provides self-generation of a sensor signal with no power supply to the device head. This simplifies the design of the sensor head, and means it can have a design which is easy to clean with no parts which are easily damaged.

In one set of examples, the device is a skin treatment device. The invention will be described in detail with reference to an implementation for a skin treatment device.

The invention makes use of charge generation induced by rubbing or contact between materials. This may be based electrostatic charging, although preferred examples make use of the triboelectric effect. The triboelectric effect is a physical phenomenon that has been known for a long time. Due to the triboelectric effect (also known as triboelectric charging, contact electrification or triboelectrification) certain materials become electrically charged after they come into contact with another different material through friction. Especially dry skin (stratum corneum) is highly triboelectrically active as often experienced in everyday life e.g. static discharges as shooting sparks when touching objects like a door handle.

The triboelectric effect is based on a series that ranks various materials according to their tendency to gain electrons (become negatively charged) or lose electrons (become positively charged). This series is for example disclosed in A. F. Diaz and R. M. Felix-Navarro, A semi-quantitative triboelectric series for polymeric materials: the influence of chemical structure and properties, Journal of Electrostatics 62 (2004) 277-290. The best combinations of materials to create static electricity are one from the positive charge list and one from the negative charge list (e.g. PTFE against copper, or fluorinated ethylene propylene (FEP) against aluminum). Skin tends to become positively charged when brought in contact with other materials. This means skin is an electron donor and on the top of the triboelectric list. The end of this list includes electron acceptors such as various rubber compounds including for example santoprene rubber, hypalon rubber, butyl rubber, ethylene propylene diene monomer (EDPM) rubber, polydimethylsiloxane (PDMS), as well as polytetrafluoroethylene (PFTE, Teflon).

For generating triboelectric charge when contact is made with the skin, the rubbers (and Teflon) listed above are examples of suitable materials, although others (such as aluminum oxide ceramic) will be known to those skilled in the art, by consulting the triboelectricity series.

The triboelectric generation process involves the conversion of mechanical energy into electrical energy through a coupling between two main physical mechanisms: contact electrification (tribocharging) and electrostatic induction.

This invention makes use of the triboelectric effect (and capacitive coupling) as a sensor principle for sensing the thickness of the top layer of a layered structure, such as the stratum corneum in the case of the skin, rather than for electricity generation or power harvesting.

With increased removal of the stratum corneum which is a compact dense and insulating layer of dead, keratin filled corneocytes the skin becomes more hydrated and potentially less electrified as more hydrated, viable epidermal skin layers are accessed. Consequently skin layer resistance decreases and electrostatic charges cannot built up.

FIG. 1 schematically shows an embodiment of the microdermabrasion device 1. The device 1 comprises a vacuum system, with a pump 2 and a channel 4. A removable device tip (a cap or head) 6 is provided. The pump 2 can suck air into the channel 4, and the channel has a channel inlet at the device head 6. The channel inlet is surrounded by a channel rim 7. This channel rim 7 facilitates gliding of the device head 6 over the skin (not shown). The device head 6 for example comprises a microdermabrasion zone configured remote from the channel inlet. The microdermabrasion zone is in the form of an abrasive ring which for example circumferentially surrounds the channel rim 7. The microdermabrasion zone includes abrasive structures such as aluminum oxide particles (20-100 µm) bonded on an outer surface.

Optionally, the head may be driven to rotate, oscillate or vibrate to assist the abrasive removal of a portion of the skin outer layer.

The device is a hand held battery operated device, and it is shown sitting on a recharging station 10. The invention is not limited to handheld devices but may also relate to split devices, i.e. for instance a device with a main part, especially for providing the vacuum, and a tube with an abrasive treatment part, that can be moved at least partly independent of the main part.

More details about this general type of device may for example be found in WO 2014/191149 and WO 2014/136013.

In accordance with this invention, the device is modified so that the head 6 functions as one electrode of a charge generator, for example a triboelectric charge generator. It comprises an abrasive ring 8 (FIG. 4) on which charges are generated. There is also an induction electrode on the back of the ring inside the device head. A handle electrode 12 is provided, as well as circuitry for measuring a parameter (for example a voltage between the ring 8 and the handle 12) which is dependent on the generated charges and the skin impedance (which determines the charge leakage). The parameter is measured using the charges generated by the generator.

The device 1 may have an output device 14 such as a display, microphone or a haptic output device, for providing output information to the user to assist them in using the device.

Figure 2:
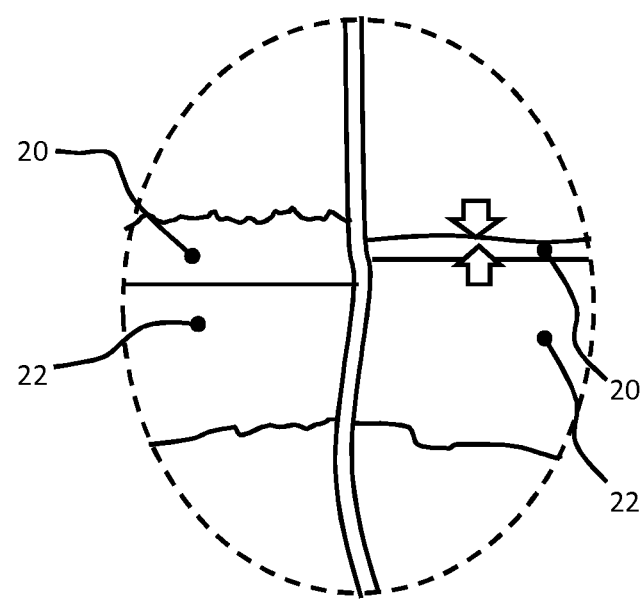
FIG. 2 shows the skin before and after treatment.

FIG. 2 shows the top two layers of the skin, namely the stratum corneum 20 and the other layers 22 of the epidermis, beneath which is the dermis. The left part shows pre abrasive treatment and the right part shows post abrasive treatment. The stratum corneum is smoothed and thinned, and the epidermis is thickened.

Preferred examples of the device of the invention use a single electrode triboelectric generator as sensor producing a triboelectric charge, to determine a value which is related to the rate and/or amount of skin exfoliation during a treatment with the skin rejuvenation device.

When the level of exfoliation is reached that offers an optimal balance between rejuvenation and the prevention of skin irritation (skin rash) a signal issued by the output device 14 tells the end user to move on to the next untreated piece of skin.

The sensor principle is based on the coupling of triboelectric effect and capacitive coupling. The rubbing of the rejuvenation device against skin causes an electrical charge build-up. The charge leaks then away through the skin. The rate of this process depends on the skin conductance.

The stratum corneum 20 is a resistive barrier for the skin conductance. Exfoliation of the stratum corneum lowers this barrier, causing the tribo-generated charge to leak away faster.

Figure 3:
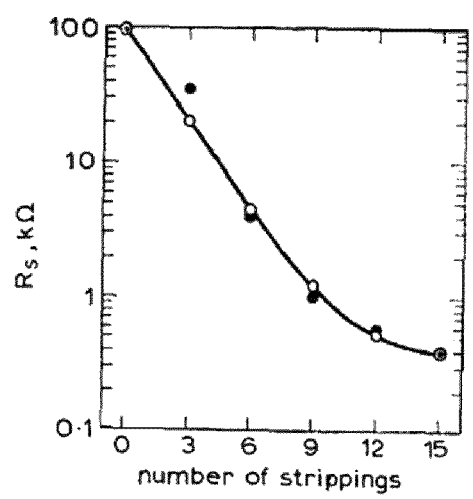
FIG. 3 shows the effect of the treatment on the skin resistance based on tape stripping.

This effect is shown in FIG. 3, which is taken from T. Yamamoto and Y. Yamamoto, Electrical properties of the epidermal stratum corneum, Medical and Biological Engineering (March 1976), pp. 151-157. It shows the resistance of the stratum corneum (y-axis) as a function of a number of tape stripping actions carried out (x-axis). The solid dots are experimental values and the open dots are theoretical values. It shows clearly the relationship between resistance and the removal of stratum corneum due to repeated tape strippings.

Figure 4:
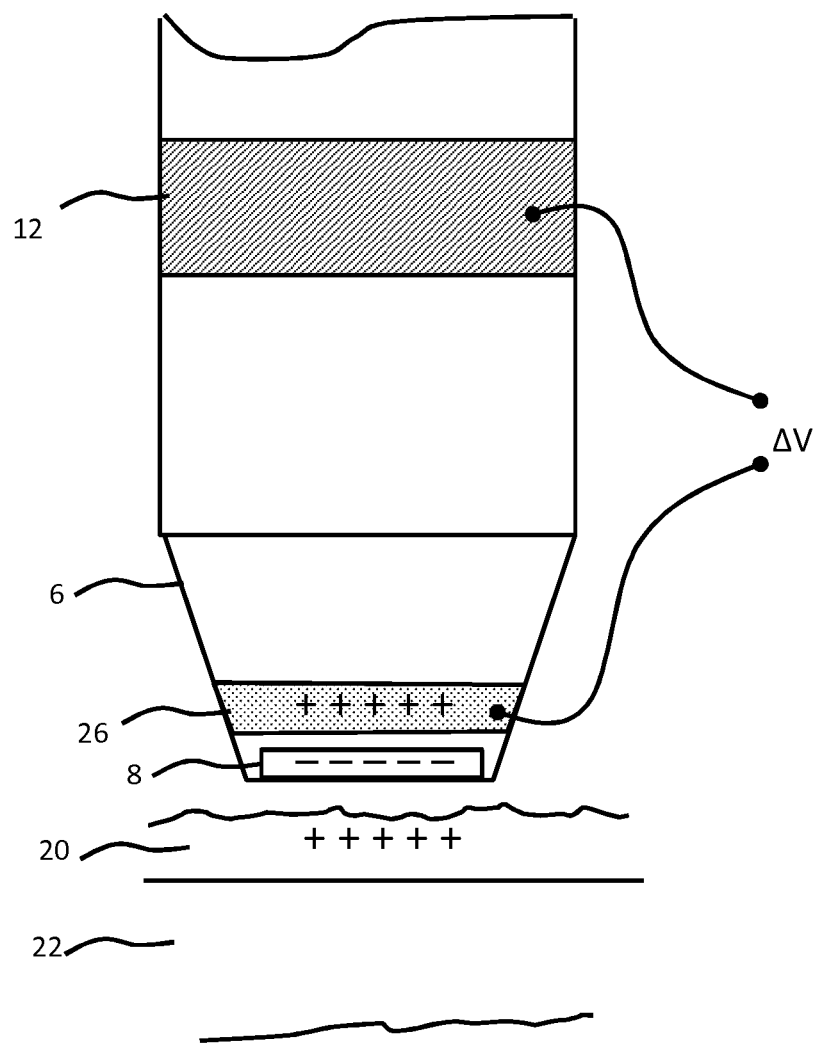
FIG. 4 shows the skin treatment device in more detail.

FIG. 4 shows an embodiment the device in more detail. A conducting ring inside the head 6 functions as a contact electrode 26 on which charges are induced, whereas the ring 8 is provided on the outside of the head, for example glued. After triboelectrification, there are positive charges at the skin surface 20 as shown. The sensing modality is based on the triboelectric effect and capacitive coupling. The triboelectrically generated voltage is shown as ΔV between the contact electrode 26 and the handle electrode 12. The handle electrode has a contact area with the hand for example of 10 to 250 $cm^2$ for example 10 to 150 $cm^2$. The contact electrode 26, in the form of a conducting ring, inside the head 6 functions as a contact or induction electrode and it responds to the surface charge build-up on the abrasive ring 8 by means of capacitive coupling. A high impedance voltage meter (e.g. >$10^{11}\Omega$) is used to measure the potential difference between the contact electrode 26 and the end user, as present at the handle electrode 12. A high impedance is used to prevent charge from leaking away via the metering circuit. The metal hand contact 12 on the handle of the device ensures a low resistance electrical contact to the end user. The size of this contact needs to be sufficient as not to disturb the measurement of the tribo generated charge. For example, a size of 10 to 150 cm$^2$ is typically appropriate. The abrasive ring is for example made out of aluminum oxide ($Al_2O_3$) ceramic particles, a material at the opposite end of the triboelectric series to skin. The contact electrode 26 is a metallic ring into which charges are induced, whereas the abrasive ring is typically an insulator. The abrasive ring 8 is however not limited to insulators. If the abrasive ring is made of a conductive material, it can also be used as the contact electrode 26. In such an example, the abrasive ring 8 and the contact electrode 26 are the same component.

The rubbing action used to perform the abrasion thus results in the generation of charges by the triboelectric effect, and these result in a voltage across the capacitance defined between the user and the abrasive ring 8 and therefore the contact electrode 26.

The charges results in temporary voltage peaks. The height of the voltage peaks observed by a sensor circuit, caused by the triboelectric effect and brought about by the scrubbing of the device against the skin, is a measure of the exfoliation of the skin. When a threshold is met, for example when the peak is lowered by a defined percentage, a signal is given to the end user to move on to the next skin spot.

In a more sophisticated example, the time derivative of the rising slope of the voltage signal may be used as a measure of stratum corneum removal. The time derivative of the voltage of the slope diminishes when the stratum corneum is removed since it is the sum of a charge build-up by the triboelectric effect brought about by a rubbing movement and the leaking away of charge through the upper skin layers to the body.

The sensed signals will be comparable for rubbing actions with equal speed and pressure. However, variations in the expected signals can be taken into account in the signal processing. The voltage may be measured using a capacitive coupling sensor, for measuring the voltage between the contact electrode 26 in the head 6 and the handle contact 12.

An example of a suitable voltage measuring circuit for measuring a capacitive coupling voltage is described in US 2008/0287767A1. Indeed, the signal measured in this previous application will be orders of magnitude smaller, so the required sensing circuitry may be somewhat simpler.

Figure 5:
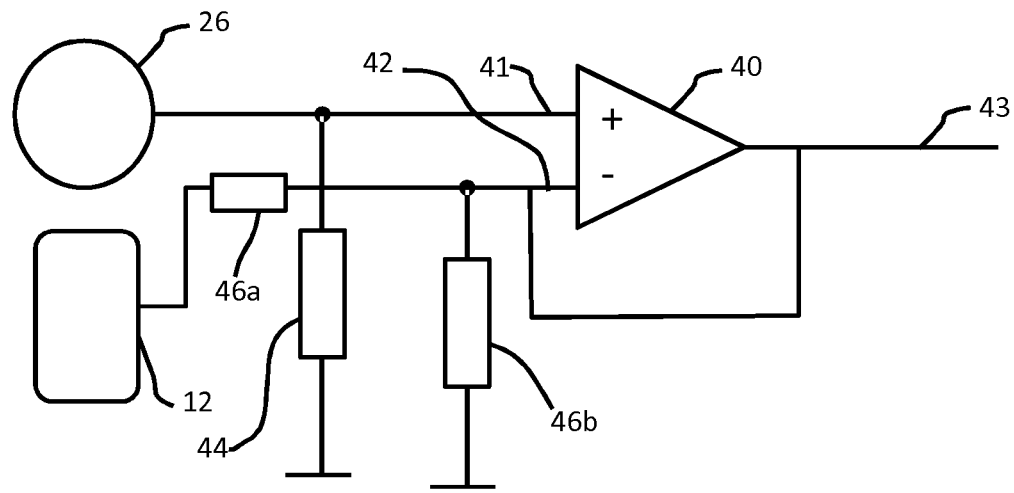
FIG. 5 shows in simplified form a voltage amplifier circuit for detecting the triboelectrically generated charge.

A basic outline of the sensor circuit is schematically shown in FIG. 5. The circuit is the input stage of a signal processing circuit for which the contact electrode 26 and handle electrode 12 provide inputs. The circuit comprises a differential amplifier 40, such as an operational amplifier, with a non-inverting input 41, an inverting input 42, and an output 43. The contact electrode 26 is connected to the non-inverting input of the amplifier 40. The amplifier has a very high input impedance, for example 200 T$\Omega$. The amplifier 40 is basically connected as a buffer amplifier, having its inverting input 42 connected to its output 43, so that the amplifier's output 43 carries the same voltage signal as the amplifier's inverting input 42. The circuitry may have further signal processing components, or the amplifier's output may be connected straight to the handle electrode 12. The output signal is interpreted by a controller, which in turn controls the output device 14 to provide feedback to the user.

In use, when placed in close proximity to a person's body, the abrasive ring 8 has a capacitive coupling with the body. The capacitance value of this coupling is typically in the order of a few pF. The input of the amplifier 40 has an input resistance which, in a suitably selected amplifier, may be approximated by infinity. However, it is desirable to provide a defined leak-resistance to zero voltage level, which is provided by a resistance 44 connected between the amplifier's positive input terminal and ground. The combination of coupling capacitance and leak-resistance forms a high-pass filter.

The elbow frequency of this high-pass filter is as low as possible, for example of the order of 0.2 Hz. This leads to a design value of 100 G$\Omega$ or higher for the input resistance 44.

The handle electrode 12 is connected to the inverting input 42 through a potential divider 46a, 46b.

There are no circuit voltages applied to the inputs 26, 12 of the amplifier. Instead, charge generated by the triboelectric effect are induced in the contact electrode 26, so that electrons flow between the contact electrode 26 and the body of the user in contact with the handle electrode 12. These charges create a measurable potential across the inputs 26, 12. The voltage changes over time as the charge leaks to the body, and the way the voltage changes is a function of the capacitance between the inputs 26,12 and the resistance of the skin, which in turn is a function of the level of skin abrasion.

Figure 6:
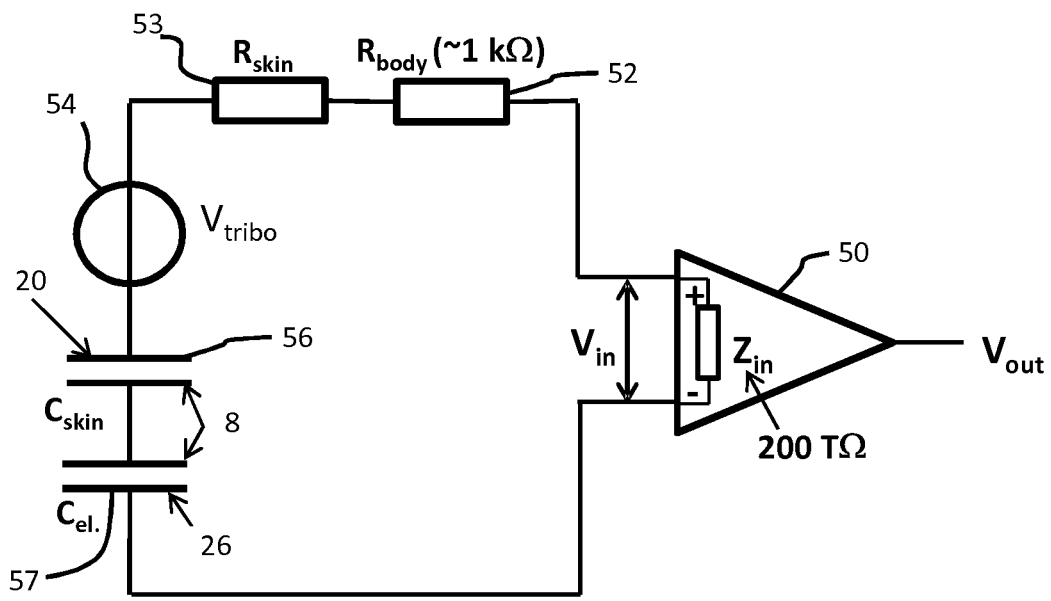
FIG. 6 shows an simplified equivalent circuit for the sensor system when in contact with the skin.

FIG. 6 shows an approximate equivalent circuit. The amplifier circuit of FIG. 5 is shown as 50. Between the inputs, there is a series connection of the body resistance 52 of approximately 1 k$\Omega$, the skin resistance 53, a voltage source 54 representing the voltage generated by the triboelectric effect, the skin capacitance 56 (between the abrasive ring 8 and skin surface) and the capacitance 57 between the ring 8 and the contact electrode 26. The readout electronics essentially comprises an amplifier 50 having a very large input impedance.

In use, triboelectrically generated charges are generated at the skin and the ring 8. The ring 8 is also capacitively coupled to the contact electrode 26. Charges are therefore inducted on the electrode.

The amplifier 50 measures the voltage difference between the handle electrode 12 (which is at the voltage potential of the user) and the contact electrode 26 in the head of the device. An amplifier with a very large input impedance is used to prevent the charges leaking away too fast to be measured.

Figure 7:
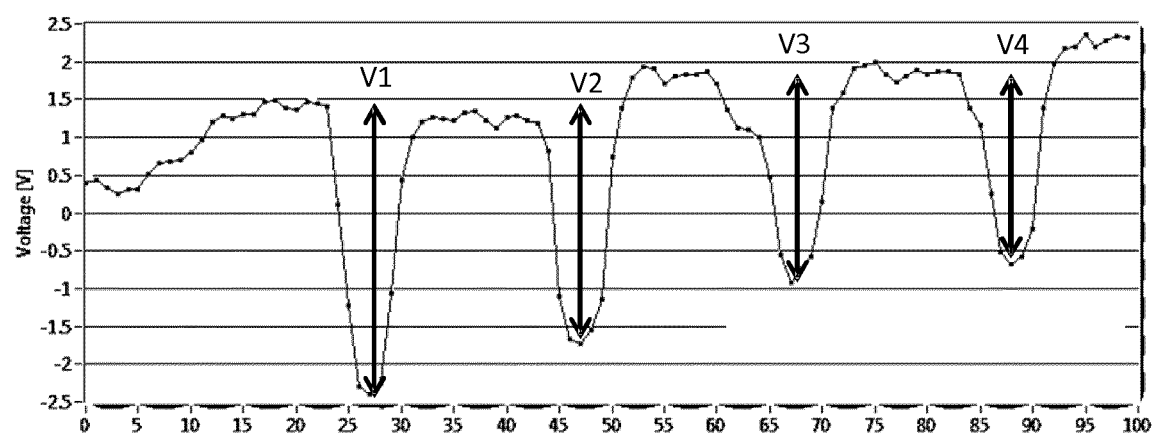
FIG. 7 shows the results of an experimental use of the system.

The system has been tested, by performing sampling of the amplifier voltage at 10 Hz. In the test, measurements of 100 samples were taken, taking 10 seconds. The results are shown in FIG. 7, which plots the voltage versus the sample number (i.e. every 0.1 s). During the first 20 samples nothing was done, and then 4 consecutive strokes of about 20 cm long were performed on the inner forearm (hairless skin area). The skin resistance is the dominating parameter in the leaking away of charge built up by the triboelectric effect, brought about by rubbing the two different materials (skin and the head 6) together. The four consecutive strokes can be seen in FIG. 7, each causing a corresponding voltage spike V1 to V4. The magnitude of the voltage spike diminishes along the sequence of consecutive strokes, indicating a faster charge leakage rate, caused by a decreased skin resistance and rising skin hydration level. This decreased skin resistance is caused by the partial abrasion of the stratum corneum by the abrasive material of the device head, thereby exposing a more hydrated skin layer to the skin surface.

The device may be calibrated to enable more accurate evaluation of the data.

A first calibration approach may take account of differences in the way the device is used, for example the stroke length and stroke speed. The device may be designed for operation with a certain stroke length, controlled contact pressure and speed, but the user may for example be able to provide, as an input, that they prefer longer or faster strokes, or shorter or slower strokes. The settings used to interpret the measured signals from the amplifier may then be adjusted accordingly.

There may also be calibration for a particular users' skin. This may be carried out by performing a test routine, whereby the user performs a number of and type of strokes which they consider suitable. By monitoring the change in electrical characteristics for these reference strokes, a threshold may then be set so that the same degree of skin abrasion may be provided in future strokes, with the device indicating to the user when the same amount of skin treatment has been completed as in the reference cycle.

To perform a system calibration check with the microdermabrasion device, testing against two suitable materials from the triboelectric series (e.g polyamide/Nylon and polyimide/Kapton, or polyamide and polyethylene, polyamide and polyester) could be carried out. For example, the user may perform multiple passes against a reference template (having two different materials) or a tape that may be applied to the skin. These reference signals are then taken and compared with an internal calibration curve to check whether the system is within specifications.

To tolerate for different users, an individual baseline reference curve may be created and then compared with a reference graph (for example from a validation study showing the relationship between tribovoltage and skin level removed). When the measured voltage dropped to for example 30% of its initial value, the treatment may be instructed to be stopped.

Another option is to learn from treatment results. The treatment duration may be monitored and the sensing data saved. This data may then be compared with reference strokes made by the user before each dermabrasion treatment. The treatment curves can also be also stored in the system to provide continuous feedback to the user and coach him or advise him on personalized device settings and a preferred treatment duration. This can be done also in combination with other skin property measurements such as skin moisture.

When the voltage is sampled at a high enough sampling rate (10 Hz or more), the stroke duration can be determined. When a stroke is performed very slowly, the triboelectrical charge does not accumulate, but leaks away through the skin. A reference stroke over a known length combined with a measured stroke duration can function as a calibration step.

It will be clear from the description above that one main area of interest is for microdermabrasion devices. However, the principles explained above may be employed for any surface treatment process which removes part of a surface layer which thereby changes the electrical charge retaining and/or generating properties of the remaining layer structure.

The term "substantially" herein, such as in in "substantially consists", will be understood by the person skilled in the art. The term "substantially" may also include embodiments with "entirely", "completely", "all", etc. Hence, in embodiments the adjective substantially may also be removed. Where applicable, the term "substantially" may also relate to 90% or higher, such as 95% or higher, especially 99% or higher, even more especially 99.5% or higher, including 100%. The term "comprise" includes also embodiments wherein the term "comprises" means "consists of". The term "and/or" especially relates to one or more of the items mentioned before and after "and/or". For instance, a phrase "item 1 and/or item 2" and similar phrases may relate to one or more of item 1 and item 2. The term "comprising" may in an embodiment refer to "consisting of" but may in another embodiment also refer to "containing at least the defined species and optionally one or more other species".

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The devices herein are amongst others described during operation. As will be clear to the person skilled in the art, the invention is not limited to methods of operation or devices in operation.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "to comprise" and its conjugations does not exclude the presence of elements or steps other than those stated in a claim. Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to". The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention further applies to a device comprising one or more of the characterizing features described in the description and/or shown in the attached drawings. The invention further pertains to a method or process comprising one or more of the characterizing features described in the description and/or shown in the attached drawings.

The various aspects discussed in this patent can be combined in order to provide additional advantages. Further, the person skilled in the art will understand that embodiments can be combined, and that also more than two embodiments can be combined. Furthermore, some of the features can form the basis for one or more divisional applications.

The invention claimed is:

1. A skin treatment device, comprising;
    a head;
    an abrasive ring disposed at an end of the head for contacting a skin surface; and
    a sensor for sensing layer removal from the skin surface, the sensor comprising: a contact electrode; a handle electrode; a circuit adapted to measure a voltage between the contact electrode and the handle electrode; a triboelectric generator for generating charge in response to movement of the abrasive ring over the skin surface, wherein the triboelectric generator is used as a sensor for measuring a parameter which is dependent on a level of layer removal, signal from the sensor comprising the charge generated by the generator; a voltage measuring circuit for measuring a voltage between the contact electrode and the skin surface; and a voltage rate measuring circuit for measuring a rate of change of the voltage between the contact electrode and the skin surface, wherein the contact electrode is shielded by a non-conduction portion, and the contact electrode is configured not to be in physical contact with a user during use of the skin treatment device.

2. The skin treatment device as claimed in claim 1, wherein the contact electrode comprises a metallic disc which functions as a passive induction electrode.

3. The skin treatment device as claimed in claim 1, wherein the abrasive ring is adapted to contact the skin.

4. The skin treatment device as claimed in claim 1, further comprising a suction system.

5. The skin treatment device as claimed in claim 1, wherein the handle electrode is configured to be in electrical contact with a user during use of the skin treatment device.

6. The skin treatment device as claimed in claim 1, wherein the handle electrode has an area of between 10 and 250 square centimeters.

7. The skin treatment device as claimed in claim 1, further comprising: an output device and a controller for controlling the output device, which is adapted to provide an output warning when the skin treatment should be ceased based on the measured parameter.

8. The skin treatment device as claimed in claim 1, wherein the abrasive ring comprises a ceramic material or rubber.

9. The skin treatment device as claimed in claim 1, wherein the contact electrode comprises a metal disc, which functions as a passive induction electrode.

10. A skin treatment device, comprising:
a head;
an abrasive ring disposed at an end of the head for contacting a skin surface; and
a sensor for sensing layer removal from the skin surface, the sensor comprising: a contact electrode; a handle electrode; a circuit adapted to measure a voltage between the contact electrode and the handle electrode; a triboelectric generator for generating charge in response to movement of the abrasive ring over the skin surface, wherein the triboelectric generator is used as a sensor for measuring a parameter which is dependent on a level of layer removal, a signal from the sensor comprising the charge generated by the generator; a voltage measuring circuit for measuring a voltage between the abrasive ring and the skin surface, wherein the abrasive ring is adapted to receive electrons from the skin caused by a triboelectric effect caused by the triboelectric generator.

11. The skin treatment device as claimed in claim 10, wherein the contact electrode comprises a metallic disc which functions as a passive induction electrode.

12. The skin treatment device as claimed in claim 10, wherein, the abrasive ring is adapted to contact the skin.

13. The skin treatment device as claimed in claim 10, further comprising a suction system.

14. The skin treatment device as claimed in claim 10, wherein the handle electrode is configured to be in electrical contact with a user during use of the skin treatment device.

15. The skin treatment device as claimed in claim 10, wherein the handle electrode has an area of between 10 and 250 square centimeters.

16. The skin treatment device as claimed in claim 10, wherein the abrasive ring comprises a ceramic material or rubber.

17. The skin treatment device as claimed in claim 10, further comprising: an output device and a controller for controlling the output device, which is adapted to provide an output warning when the skin treatment should be ceased based on the measured parameter.

18. The skin treatment device as claimed in claim 10, wherein the contact electrode comprises a metal disc, which functions as a passive induction electrode.

19. The skin treatment device as claimed in claim 10, wherein the sensor further comprises a voltage rate measuring circuit for measuring a rate of change of the voltage between the contact electrode and the skin surface.

* * * * *